(12) United States Patent
Kent et al.

(10) Patent No.: US 7,075,023 B2
(45) Date of Patent: Jul. 11, 2006

(54) PUSHBUTTON MECHANICAL LIMITER SWITCH INCLUDING MOVABLE CONTACT LOCATED IN HOUSING PASSAGE WAY

(75) Inventors: Harold B. Kent, Portola Valley, CA (US); James J. LeVante, Redwood City, CA (US); Aaron T. Fine, Mountain View, CA (US)

(73) Assignee: Medconx, Inc., Santa Clara, CA (US)

( * ) Notice: Subject to any disclaimer, the term of this patent is extended or adjusted under 35 U.S.C. 154(b) by 0 days.

(21) Appl. No.: 10/819,906

(22) Filed: Apr. 6, 2004

(65) Prior Publication Data

US 2004/0245079 A1    Dec. 9, 2004

Related U.S. Application Data

(63) Continuation-in-part of application No. 10/739,252, filed on Dec. 17, 2003, now Pat. No. 6,846,996.

(60) Provisional application No. 60/434,297, filed on Dec. 17, 2002.

(51) Int. Cl.
*H01H 1/06* (2006.01)

(52) U.S. Cl. .................. 200/276; 200/275; 29/622; 29/848

(58) Field of Classification Search ............... 200/8 R, 200/8 A, 275, 276.1, 276, 290, 520–536, 200/51 R–51.17; 29/622, 848, 831
See application file for complete search history.

(56) References Cited

U.S. PATENT DOCUMENTS

| | | | | |
|---|---|---|---|---|
| 3,226,496 A | * | 12/1965 | Seabury, Jr. | ............... 200/8 R |
| 3,548,137 A | * | 12/1970 | Podgorski et al. | .......... 200/276 |
| 4,284,862 A | * | 8/1981 | Overman et al. | ........... 200/276 |
| 4,313,685 A | * | 2/1982 | Stahl et al. | .................. 200/520 |
| 4,533,803 A | * | 8/1985 | Beller et al. | ................. 200/290 |
| 6,204,463 B1 | | 3/2001 | Stringos | |
| 6,846,996 B1 | * | 1/2005 | Kent et al. | ............... 200/276.1 |
| 2001/0018918 A1 | | 9/2001 | Burnside et al. | |
| 2003/0233087 A1 | | 12/2003 | Chen | ......................... 606/41 |
| 2001/0245079 | | 12/2004 | Harold et al. | |

FOREIGN PATENT DOCUMENTS

WO    WO 01/80932    11/2001

OTHER PUBLICATIONS

International Search Report, PCT/US05/011779, (Jun. 28, 2005).

* cited by examiner

*Primary Examiner*—Michael Friedhofer
*Assistant Examiner*—Lisa Klaus
(74) *Attorney, Agent, or Firm*—Jones Day

(57) ABSTRACT

A mechanical limiter switch device, having: a housing with a slot passing at least partially therearound, the slot forming a plurality of teeth in a side of the housing; a plunger movable within the housing; a biasing mechanism configured to urge the plunger in a proximal direction within the housing; a contact member extending through the slot in the side of the housing, the contact member being configured to advance past at least one of each of the plurality of teeth in the slot each time the plunger is moved back and forth within the housing. The contact member may perform a switching function.

41 Claims, 7 Drawing Sheets

PUSHBUTTON MECHANICAL LIMITER SWITCH INCLUDING MOVABLE CONTACT LOCATED IN HOUSING PASSAGE WAY

RELATED APPLICATION

This application claims priority under 35 U.S.C. Section 119 to U.S. Provisional Application No. 60/434,297 entitled Mechanical Use Limitation Switch and filed on Dec. 17, 2002; and is a Continuation-in-Part of U.S. application Ser. No. 10/739,252, filed on Dec. 17, 2003, now U.S. Pat. No. 6,846,996, the full disclosures of which are incorporated herein by reference in their entirety for all purposes.

TECHNICAL FIELD

In general, the present invention relates to mechanical devices that limit the number of times an electrical device can be used. In particular, the present invention relates to mechanical switches that prevent medical devices from being used more than a few times.

BACKGROUND OF THE INVENTION

Use-Limiter devices are used to prevent medical devices from being used more than the pre-determined number of uses designated by the manufacturer. For example, it may be desirable that a typical medical device is only operated three to five times. Once the device has reached the manufacturer's specific number of uses, then the device is permanently disabled and cannot be reused, reconditioned or refurbished in any way. After that, the device should be disposed of for reasons of patient safety.

Typically, such limiter devices comprise electrical circuits with associated software. These systems permit a medical device to be plugged in into a power supply such that it will operate only several times. After that, the medical device will not operate when plugged back into the power supply.

Problems with such systems include the fact that they typically include electrical controllers. Installing such electrical controllers may necessitate retrofitting both the controller, and the medical device itself. A further problem common to such systems is that they rely on integrated circuits, and that the memories of such integrated circuits may be damaged by typical sterilization procedures, such as X rays.

SUMMARY OF THE INVENTION

The present invention provides a mechanical limiter device that can be used to either open or close a circuit, and/or change the inductance, capacitance, and/or resistance of an electrical system.

In preferred embodiments, the present invention provides a mechanical use-limiting device, including: a housing having a slot passing at least partially therearound, the slot forming a plurality of teeth in a side of the housing; a plunger movable within the housing; a biasing mechanism configured to urge the plunger in a proximal direction within the housing; and a contact member extending through the slot in the side of the housing, the contact member being configured to advance past at least one of each of the plurality of teeth in the slot each time the plunger is moved back and forth within the housing. In preferred aspects, the number of times the device can be activated equals the number of teeth in the slot in the side of the housing.

In preferred aspects, the biasing mechanism is a spring, and the contact member is an end of the spring. Also in preferred aspects, the spring is receivable into the housing through a side channel in the housing. In preferred aspects, the housing may comprise separate first and second portions, wherein the slot is formed in a space between the separate first and second portions.

In preferred embodiments, the housing is slidably received onto a pair of carrier pins which are in turn mounted on a printed circuit board. A flex circuit may optionally be mounted onto the printed circuit board.

In other preferred embodiments, the housing comprises: an inner portion made of an electrically non-conducting material; and an outer portion made of an electrically conducting material. In these embodiments, the slot in the housing may be formed solely by the outer portion of the housing.

The present invention also provides a method of limiting the number of uses of an electrical device, by: advancing a biased plunger into a housing of a mechanical limiter device each time the electrical device is activated, and allowing the biased plunger to retract from the housing each time the electrical device is de-activated, wherein the mechanical limiter device has a contact member extending through a slot in the side of its housing, the slot forming a series of teeth, wherein the contact member is configured to advance past at least one of each of the plurality of teeth in the slot each time the plunger is moved back and forth within the housing.

The present invention also provides a method of forming a mechanical limiter device, by: injection molding a first portion of a housing; injection molding a second portion of the housing; assembling the first and second portions of the housing together; inserting a spring into the housing; and inserting a plunger into the housing, the plunger being received within the spring.

A first advantage of the present invention is that it is not damaged by typical sterilization procedures, such as Gamma, ETO, E-Beam, AutoClave, etc.

A second advantage of the present invention is that it is physically small, but can be easily assembled for use inexpensively and in a short period of time.

DETAILED DESCRIPTION OF THE DRAWINGS

The present invention claims priority to U.S. application Ser. Nos. 60/434,297 and 10/739,252, the full disclosures of which are incorporated herein by reference in their entirety for all purposes. As such, various features of the operation of the present invention can be fully understood by reference to the Ser. Nos. 60/434,297 and 10/739,252 patent applications. For example, basic operation of a mechanical limiter device can be understood by referring to FIGS. 1 to 4, and associated description, of application Ser. No. 10/739,252. Further details of the operation of various mechanical limiter device embodiments of the invention are seen in FIGS. 5a to 11b of application Ser. No. 10/739,252.

However, the present invention provides a number of novel and non-obvious improvements over the Mechanical Limiter Switch as disclosed in U.S. patent application Ser. No. 60/434,297 and U.S. application Ser. No. 10/739,252.

The present invention provides a mechanical limiter device which is used for shutting off an electrical device after it has been used a pre-determined number of times. The present system is particularly useful with medical devices since such devices should only be operated a small number of times before they are disposed.

FIGS. 1 to 3B show preferred embodiments of a mechanical limiter device having a one or two-part housing, with the housing received onto a pair of carrier pins.

Figure 4A:
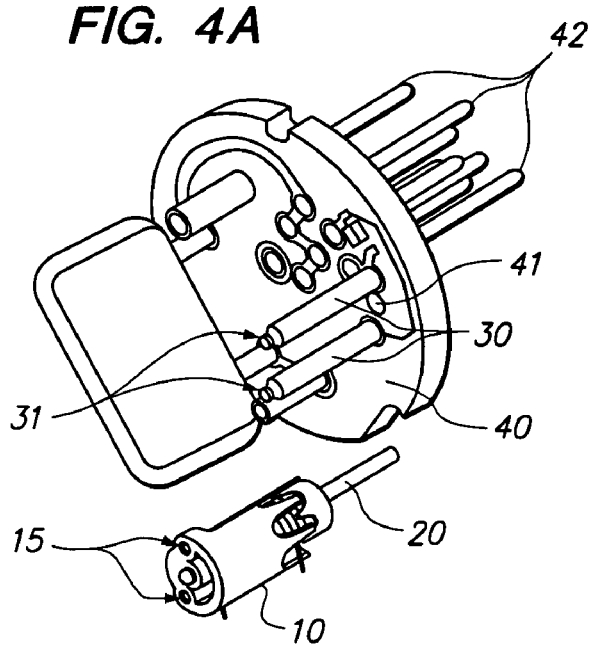
FIG. 4A is a perspective view of the mechanical limiter device of FIG. 1, positioned for mounting onto a printed circuit board.
Figure 4B:
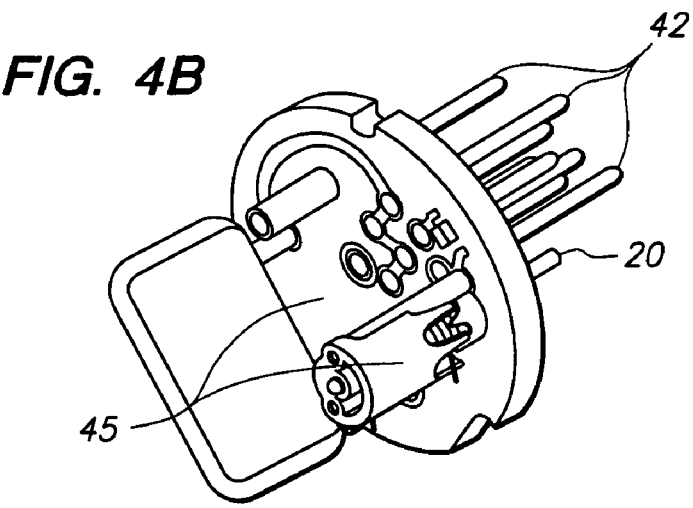
FIG. 4B is a perspective view of the mechanical limiter device of FIG. 1, integrally formed into a printed circuit board.
Figure 4C:
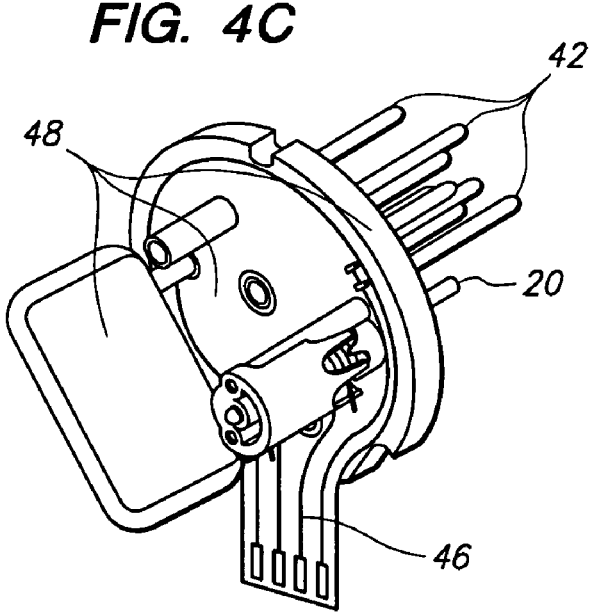
FIG. 4C is a perspective view of the mechanical limiter device of FIG. 1, positioned for receipt onto a printed circuit board, with a flex circuit also disposed on the printed circuit board.

FIGS. 4A to 4C show various embodiments of the mechanical limiter device mounted to, or formed integral with, a printed circuit board.

Figure 5:
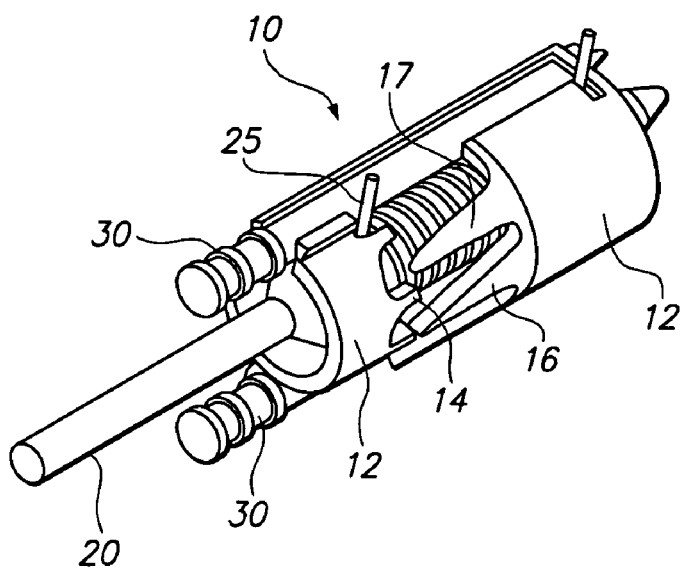
FIG. 5 is a perspective view of an embodiment of the invention having an electrically conductive material coating the teeth of the slot.

FIG. 5 shows an embodiment of the mechanical limiter device with an electrically conductive coating on the teeth of the device.

FIGS. 6 to 9 show an embodiment of the mechanical limiter device having a two-part housing, with separate inner and outer portions, and with the slot formed in the outer portion of the housing.

Figure 10A:
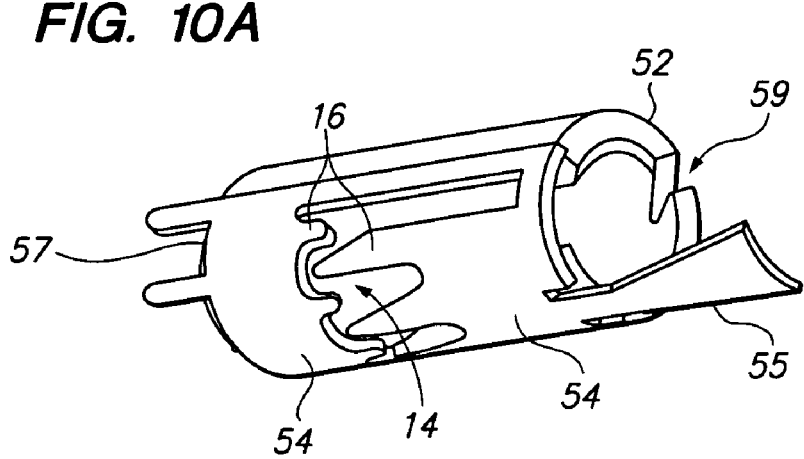
FIG. 10A is a first perspective view of an embodiment of the invention having a cut-out section near the distal end of the outer portion of the housing, for retention of a spring after loading.
Figure 10B:
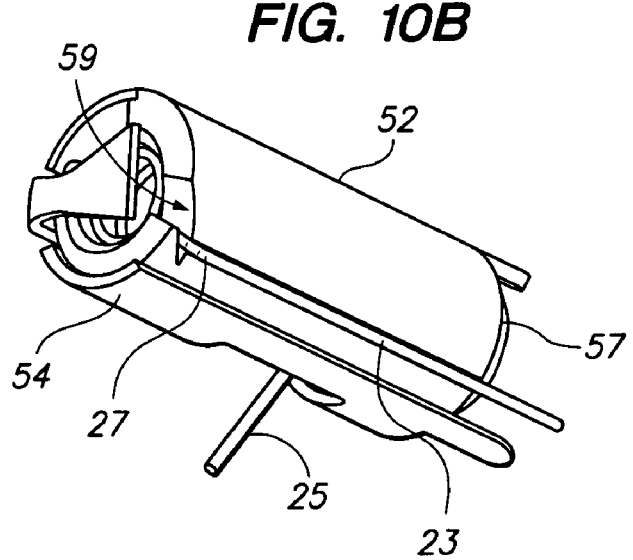
FIG. 10B is a second perspective view of the embodiment of the invention having a cut-out section near the distal end of the outer portion of the housing, showing a spring received therethrough, for retention of a spring after loading.

FIGS. 10A and 10B show an embodiment of the mechanical limiter device having a cut-out section near the distal end of the outer portion of the housing, for receiving a spring therein.

Figure 11A:
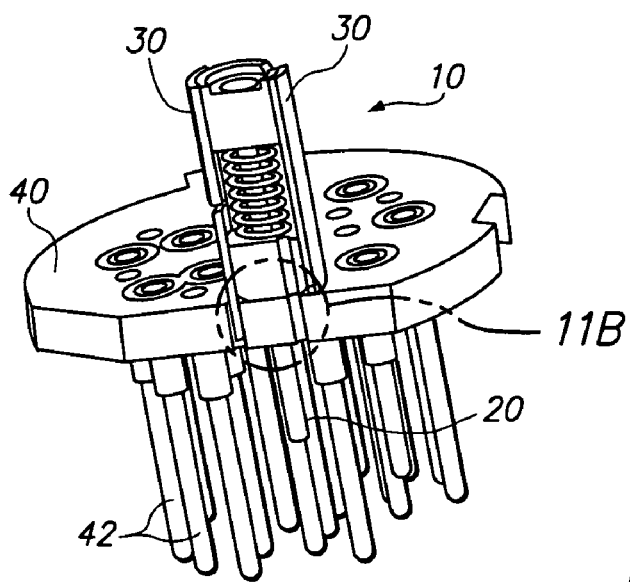
FIG. 11A is a perspective view of an embodiment of the present invention mounted onto a printed circuit board.
Figure 11B:
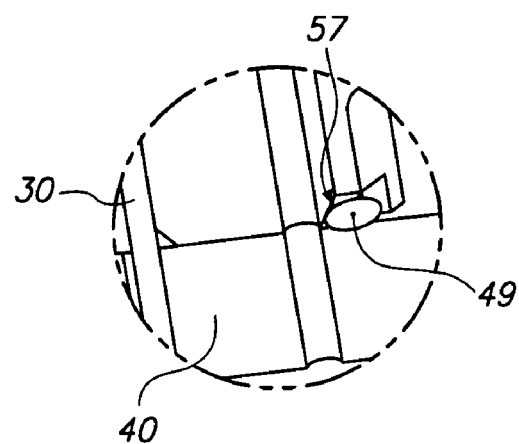
FIG. 11B is a close-up view of a portion of the device shown in FIG. 1A, showing a chamfered edge on the outer surface of the housing, with a solder meniscus adjacent thereto.

FIGS. 11A and 11B show an embodiment of the mechanical limiter device mounted onto a printed circuit board with a chamfered edge on the outer surface of the housing.

Figure 12A:
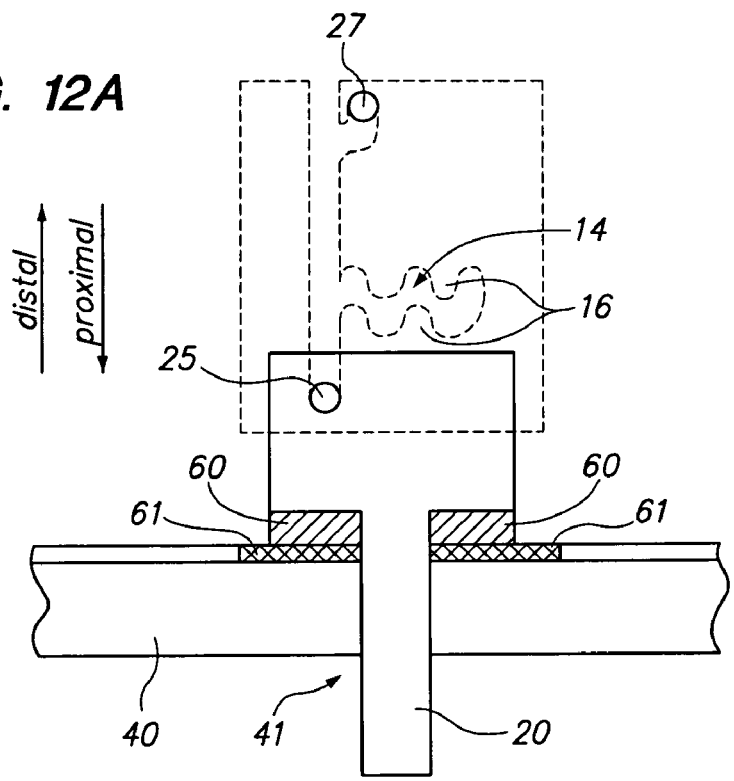
FIG. 12A is a schematic illustration of the limiter device prior to use.

FIG. 12A is a schematic illustration of an optional embodiment of the present limiter device prior to use.

Figure 12B:
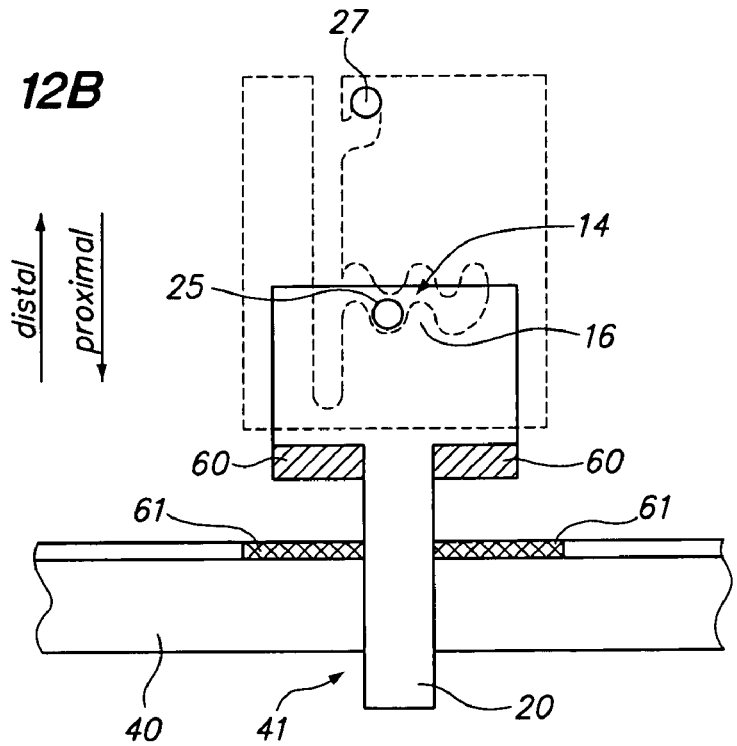
FIG. 12B is a schematic illustration of the limiter device in use.

FIG. 12B is a schematic illustration of an optional embodiment of the present limiter device in use.

Figure 1:
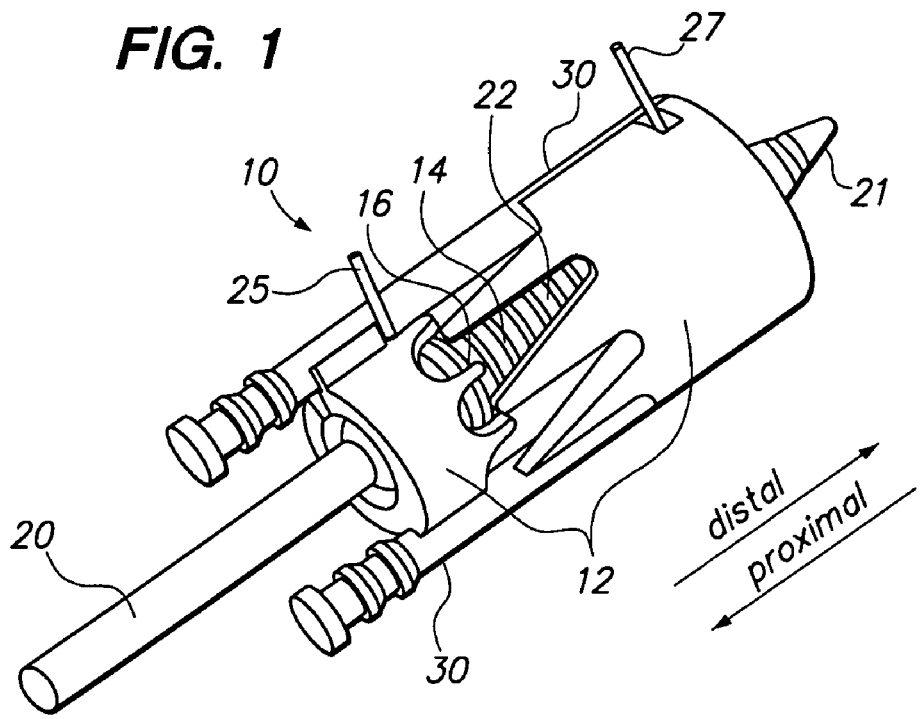
FIG. 1 is a perspective view of a first embodiment of the present invention having a one piece housing, wherein the spring is loaded distally.

Referring first to FIG. 1, a mechanical limiter device 10 is provided. Device 10 includes a housing 12 having a slot 14 passing at least partially therearound. As can be seen, slot 14 forms a plurality of teeth 16 in a side of housing 12. A plunger 20 is movable back and forth within housing 12.

A biasing mechanism (e.g. spring 22) is configured to urge plunger 20 in a proximal direction within housing 12. A contact member 25 extends through slot 14 in the side of housing 12. Contact member 25 is configured to advance past at least one of each of the plurality of teeth 16 in slot 14 each time plunger 20 is moved in either the proximal or distal direction within housing 12. In accordance with the present invention, contact member 25 therefore rotates partially around housing 12 each time plunger 20 is advanced. Each time an associated medical device is activated (e.g.: plugged into its power supply), plunger 20 is depressed (i.e.: moved in a distal direction). Each time an associated medical device is de-activated (e.g.: unplugged from its power supply), plunger 20 springs back in a proximal direction. With each use of the medical device, contact member 25 advances along through slot 14, rotating around housing 12. Eventually, contact member 25 will move into contact with a stationary contact pin or member (not shown) which will either open or close a circuit so as to prevent the medical (or other electrical) device from being re-used. Thus, the number of times the device can be activated equals the number of pairs of teeth 16 in slot 14 in the side of housing 12.

Further details of this operation are shown in FIGS. 1 to 4, and associated description, of U.S. patent application Ser. No. 10/739,252, incorporated herein in its entirety for all purposes.

As will be further explained, housing 12 may be received onto a pair of carrier pins 30. As will be further explained, carrier pins 30 may be used to mount limiter device 10 onto a printed circuit board. Mounting of the device to the carrier pins 30 can be done by slip-fit mounting, by press-fit mounting, snap fit, soldered, crimped or glued. IE: by inserting the carrier pins 30 distally through holes in the sides of the housing, or by snapping carrier pins 30 directly into recesses in the sides of the housing.

In preferred embodiments, biasing mechanism 22 is a spring (as shown) and contact member 25 is an end (e.g. the proximal end) of the spring (as shown). It is to be understood, however, that alternate biasing mechanisms may be used instead of a spring, all keeping within the scope of the present invention. It is to be further understood that contact member 25 need not be part of a spring, and that, in the case where contact member 25 is part of spring 22, contact member 25 need not be positioned at the proximal end of the spring. For example, contact member 25 may alternately be positioned at a mid point of the spring, or even at a distal end of the spring.

Figure 2:
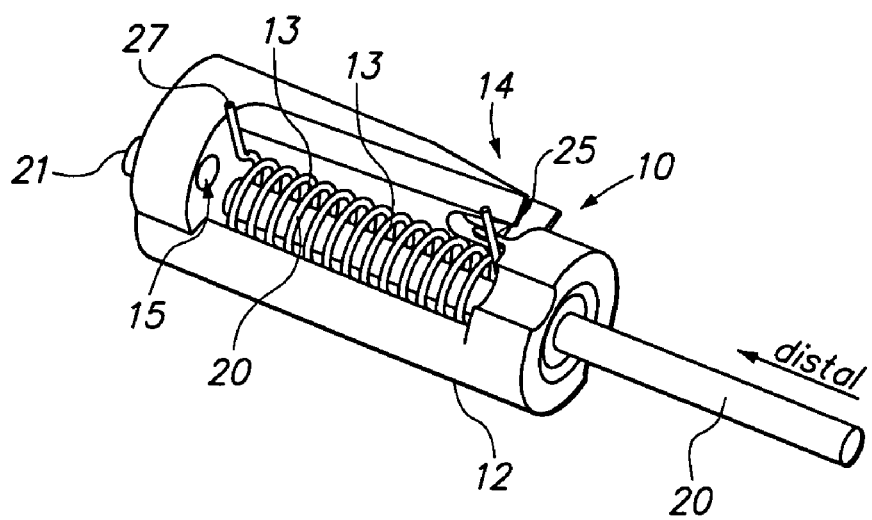
FIG. 2 is a perspective view of another embodiment of the invention having a one-piece housing, wherein the spring is loaded through the side of the housing.

FIG. 2 shows a side perspective view of another embodiment of device 10 with carrier pins 30 removed. As can be seen, spring 22 is receivable into housing 12 through a large side channel 13 in housing 12. Specifically, spring 22 is inserted into housing 12 through side channel 13 with the proximal end of spring 22 forming contact member 25, and the distal end 27 of spring 22 positioned at the distal end of side channel 13. After spring 22 has been inserted into housing 12 through side channel 13, plunger 20 may then be advanced through the center of spring 22 to assemble the device. As can also be seen in FIGS. 1 and 2, the distal end 21 of plunger 20 may be barbed (and protrude through a small hole in the distal end of housing 12). As such, once plunger 20 has been advanced through the center of spring 22, with its distal end 21 projecting out through the distal end of housing 12, the barbed distal end 21 of plunger 20 will prevent removal of plunger 20 from housing 12, thus ensuring that spring 22 is always properly positioned in side housing 12. Afterwards, device 10 may be mounted onto carrier pins 30, with one of carrier pins 30 covering side channel 13 in housing 12. An advantage of the design of the present invention illustrated in FIGS. 1 and 2 is its ease of assembly.

In various embodiments of the invention, distal end 27 of spring 22 may also act as an electrical contact point. Moreover, in various embodiments of the invention, one of carrier pins 30 may act as an electrical contact point. Specifically, contact member 25 may be rotated into a final position where it contacts one of carrier pins 30. As will be explained, in other embodiments, contact member 25 may be rotated into a final position where it contacts some other contact pin or member to open or close an electrical circuit.

Figure 3A:
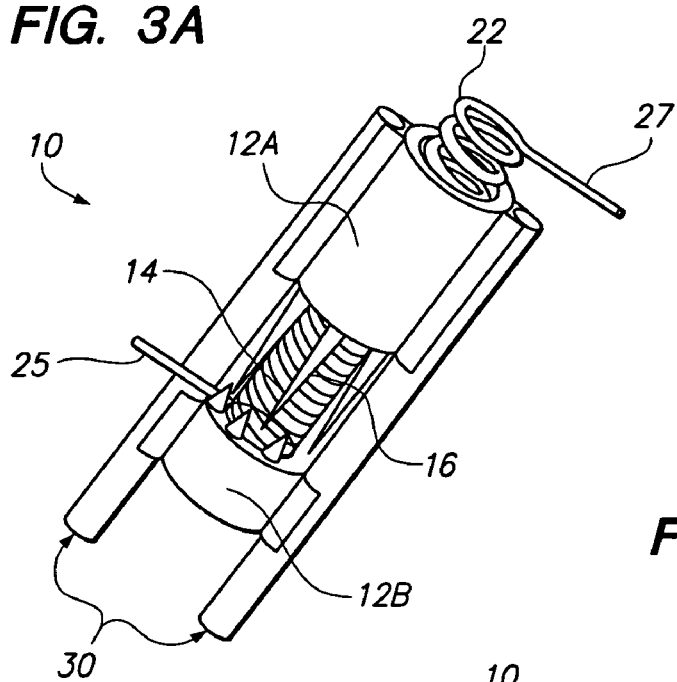
FIG. 3A is a perspective view of a second embodiment of the present invention having a two piece housing.
Figure 3B:
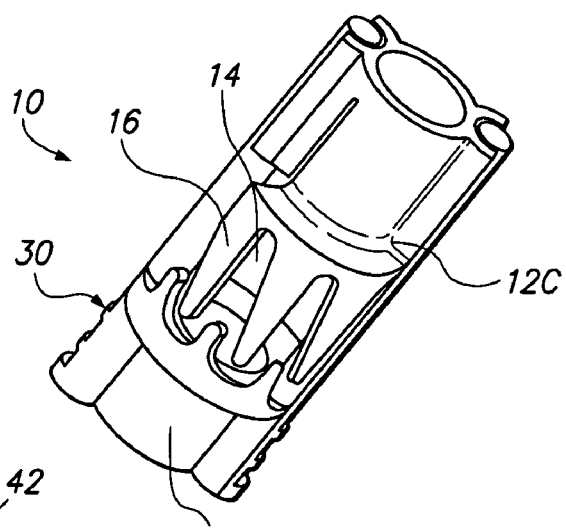
FIG. 3B is a perspective view of a another embodiment of the present invention having a two piece housing.

FIGS. 3A and 3B show embodiments of the invention having a two-part housing, as follows. Device 10 in FIG. 3A has housing 12 made from separate first and second portions 12A and 12B, respectively. As can be seen, portion 12A is the distal portion of the housing and portion 12B is the proximal portion of the housing. Portions 12A and 12B are both mounted sequentially onto carrier pins 30. In this embodiments, slot 14 is formed in the space between portions 12A and 12B. A similar arrangement is shown in FIG. 3B, where portion 12C is the distal portion of the housing and portion 12D is the proximal portion of the housing.

An advantage of the design of the present invention as shown in FIGS. 3A and 3B is that portions 12A and 12B, or 12C and 12D, can be made of different materials. For example, one portion may be made of an electrically conducting material (e.g.: metal), while the other portion may be made of an electrically insulating material (e.g.: plastic). Alternatively, both portions may be made of the same material. For example, both may be made by injection molding plastic. If molded simultaneously, an off-set injection molding process can be used. Accordingly, the housing of the present invention may be manufactured inexpensively and at low cost. When assembling the devices shown in FIGS. 3A and 3B, the spring is loaded between portions 12A and 12B, or 12C and 12D, respectively.

FIG. 4A shows an embodiment of device 10 positioned to be mounted onto a printed circuit board 40. Specifically, a pair of carrier pins 30 are first positioned on printed circuit board 40. Preferably, carrier pins 30 have barbed tips 31. Device 10 is slidably received down onto carrier pins 30 with barbed tips 31 projecting through side apertures 15 in the housing. (Side apertures 15 are also seen in FIG. 2).

When device 10 is thus secured onto printed circuit board 40, the distal end of plunger 20 will protrude through an opening 41 in the printed circuit board 40. When the associated medical (or electrical) device is activated, it will be plugged into printed circuit board 40, causing plunger 20 to be moved in a distal direction, thus initiating the functioning of the mechanical limiter device 10. (Additional electric contact pins 42 in electrical contact with printed circuit board 40 are shown for comparison).

FIG. 4B shows an alternate embodiment of the invention in which housing of the mechanical limiter device and the printed circuit board are integrally formed with one another together as a single block 45. For example, the printed circuit board and the limiter device housing may be injection molded as a single, inseparable, body.

FIG. 4C shows an alternate embodiment of the invention in which the housing of the mechanical limiter device and the printed circuit board and a flex circuit 46 are all formed together as a single unit 48. Such system advantageously provides various mounting pins and surface mount components.

FIG. 5 shows an embodiment of the invention wherein teeth 16 are coated by an electrically conductive material 17 (which may include metalized plastic). The remainder of housing 12 may optionally be made of non-conducting plastic. An advantage of this design is that contact member 25 can be maintained in electrical contact with carrier pins 30 during its progress along slot 14 past each of teeth 16. (In various alternate embodiments, electrical contact of contact member 25 does not occur until contact member 25 moves into its final position in slot 14).

FIGS. 6 to 10B show an embodiment of the invention in which limiter device 50 also has a two-part housing. In this embodiment, the housing comprises an inner portion 52 and an outer portion 54. Preferably, the inner portion 52 is made of an electrically non-conducting material, and the outer portion 54 is made of an electrically conducting material. In this embodiment, the slot 14 (and teeth 16) in the housing are formed solely by the outer portion 54 of the housing, as shown. Optionally, outer portion 54 of the housing comprises a bendable tab 55 at its distal end.

Figure 6:
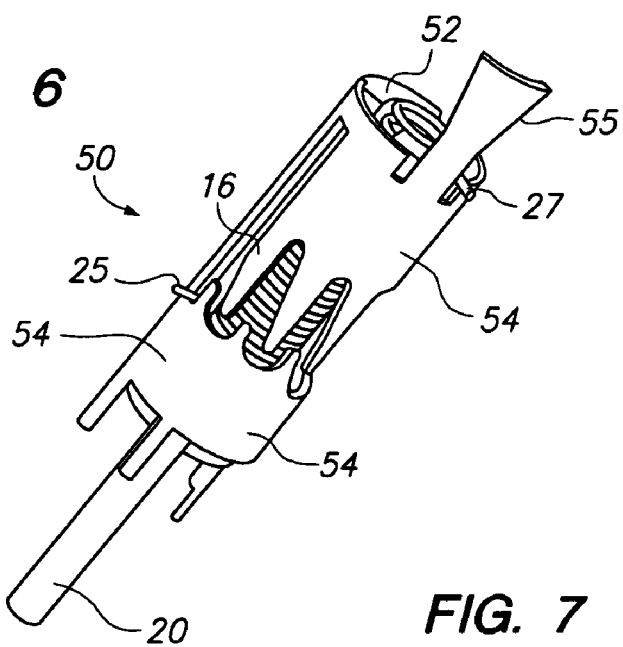
FIG. 6 is a perspective view of an embodiment of the invention having a housing with inner and outer portions, the outer portion having a bendable tab at its distal end.
Figure 7:
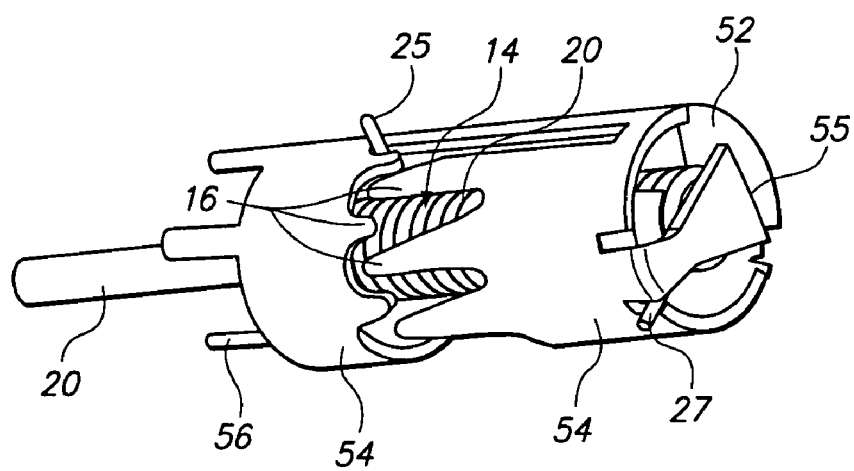
FIG. 7 is a second perspective view of the device of FIG. 6, with the tab bent to hold the distal ends of the inner portion of the housing and the spring.

Tab 55 is configured to hold the distal end of the biasing mechanism against movement of plunger 20. Tab 55 also secures inner portion 52 of the housing. As shown in FIG. 6, tab 55 is formed into outer portion 54 of the housing, initially projecting in a distal direction. As shown in FIG. 7, once inner portion 52 is received into outer portion 54, tab 55 is bent down. Thereafter, spring 22 is loaded into the device (in a manner as described above). Tab 55 will then hold the distal end 27 of spring 22 in position as the spring expands. An advantage of this design is that it replaces the need for additional components such as a cap to hold the spring in place. In addition, tab 55 provides electrical contact with distal end 27 of spring 22.

Figure 8A:
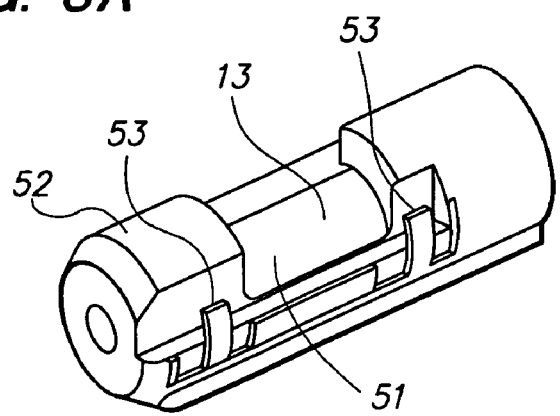
FIG. 8A is a perspective view of the inner portion of the housing of the device of FIGS. 6 and 7 prior to receiving a contact pin therein.
Figure 8B:
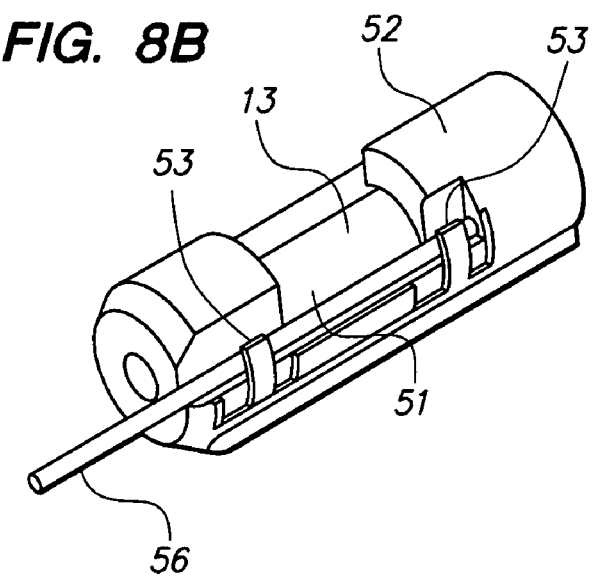
FIG. 8B is a perspective view of the inner portion of the housing of the device of FIGS. 6 and 7 after receiving a contact pin therein.

FIGS. 8A and 8B show further details of the structure of the inner portion 52 of the housing. A pair of tabs 53 may be formed into inner portion 52. As shown in FIG. 8B, an electrical contact pin 56 may be secured to inner portion 52 by tabs 53. In preferred embodiments, tabs 53 may be bendable, to further hold electrical contact pin 56 in a fixed stationary position within device 50. Such bendable tabs avoid the need for adhesives to retain contact pin 56 in place. Inner portion 52 of the housing also has a side opening 13 in which spring 22 is received (as was described with respect to FIG. 2, above). In addition, inner portion 52 has a wide window area 51 (contiguous with side opening 13) through which contact member 25 rotates. An advantage of having a wide window area 51 in inner portion 52 is that the same inner portion 52 may be used with a variety of different outer portions 54, each having different tooth and slot patterns therein.

In accordance with this embodiment of the invention, contact member 25 touches stationary contact pin 56 when contact member 25 has advanced past each of the plurality of teeth 16 in slot 14. IE: when contact pin 56 reaches its final position at the end of slot 14. (The proximal end of contact pin 56 is also shown in FIG. 7). As such, contact pin 56 adds the option of either opening or closing the circuit. Moreover, contact pin 56 further advantageously adds structural integrity to the device.

Figure 9:
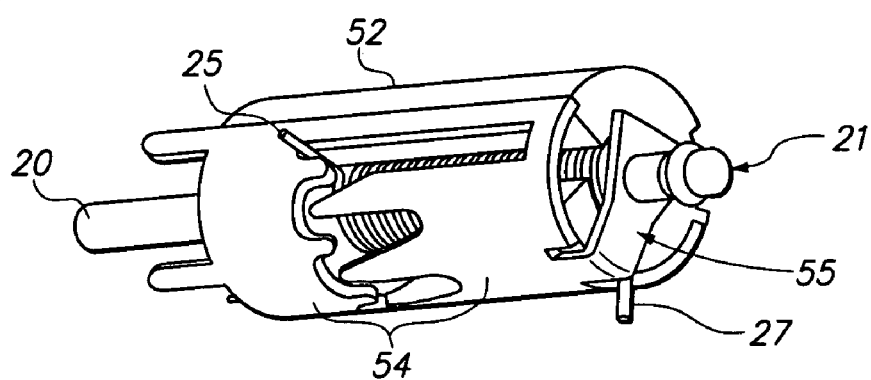
FIG. 9 is a perspective view of an embodiment of the invention similar to that shown in FIG. 6, but with the plunger extending through the tab at the distal end of the housing.

FIG. 9 shows an embodiment of the invention in which the distal end 21 of plunger 20 is received through a hole in bendable tab 55. An advantage of this embodiment of the invention is that it provides coaxial stability to the device.

FIGS. 10A and 10B show a further embodiment of the invention having a cut-out section 59 near the distal end of outer portion 54 of the housing. As shown in FIG. 10B, cut-out section 59 is dimensioned to receive a distal end 27 of a spring therein. As illustrated, the contact member 25 is formed by the proximal end of the spring. As also shown in FIG. 10B, a leg 23 of spring 22 may optionally pass along the outer surface of inner portion 52 of the housing. An advantage of this design is that device 50 may be plugged directly into printed circuit board 40, saving assembly time and avoiding the need for additional parts.

FIGS. 11A and 11B show a proximal end of the inner portion of the housing having a chamfered edge 57 (also seen in FIGS. 10A and 10B). An advantage of chamfered edge 57 is that it allows a solder meniscus 49 to form when soldering the outer portion 54 of the housing to the surface of printed circuit board 40.

FIGS. 12A and 12B show an additional optional feature of the present invention which prevents an operator from using a medical (or other electrical) device without activating device 10 (or 50). Specifically, since an operator may realize activation of the present limiter device requires plunger 20 to be depressed, (s)he may be tempted to simply cut off the proximal end of plunger 20 (i.e.: the portion of the plunger projecting through opening 41 in printed circuit board 40) in the hopes that the limiter device is not activated.

As shown in FIG. 12A, the proximal end of plunger 20 may include an electrical contact 60 thereon. Printed circuit board 40 may include an electrical contact 61 thereon. As can be seen, prior to use, electrical contacts 60 and 61 touch one another. (Such contacts 60 and 61 may be used to short out the associated medical device prior to use). A portion of the housing of the limiter device (10 or 50) is shown in dotted lines. Slot 14 and teeth 16 are also shown in dotted lines.

As shown in FIG. 12B, plunger 20 is depressed (i.e.: moved distally) to activate the limiter device (10 or 50) and thus turn on the associated medical device. As explained above, contact member 25 moves along through slot 14 past the first tooth 16 when plunger 20 is depressed. As can be seen, this movement causes electrical contact 60 and 61 to separate. Consequently, the associated medical device is no longer shorted out.

As can be seen, should an operator initially cut the proximal end of plunger 20 off, hoping to avoid the activation of the limiter device, the device will simply remain in the position shown in FIG. 12A, with electrical contacts 60 and 61 shorting out the system.

In additional embodiments, patterning of conductive and non-conductive portions of teeth 16 may also be used to prevent an operator from avoiding activation of the limiter device (by cutting off the proximal end of plunger 20) once contact member 25 has been advanced past the first tooth in slot 14. IE: once electrical contacts 60 and 61 have been separated.

In a further aspect of the present invention, a method of limiting the number of uses of an electrical device is provided. Such electrical device may include, but is not limited to, a medical device. As shown throughout the attached figures, such method may include distally advancing a biased plunger 20 into a housing 12 of a mechanical limiter device 10 each time the electrical device is activated. The biased plunger 20 retracts (proximally) from the housing 12 each time the electrical device is de-activated. In this preferred method, the mechanical limiter device 10 has a contact member 25 extending through a slot 14 in the side of the housing 12, with slot 14 forming a series of teeth 16, wherein contact member 25 is configured to advance past one of each of the plurality of teeth 16 in slot 14 each time plunger 20 is moved back and forth within the housing. In preferred aspects of this method, movement of plunger 20 back and forth within housing 12 causes contact member 25 to advance into contact with a contact pin or member, thereby either completing or shorting out an electrical circuit.

In a further aspect of the present invention, a method of forming a mechanical limiter device is provided. Such method may include injection molding a first portion (12A or 52) of a housing; injection molding a second portion of the housing (12B or 54); assembling the first and second portions of the housing together; inserting a spring 22 into the housing; and inserting a plunger 20 into the housing, plunger 20 being received within spring 22.

In preferred aspects of the method, the first and second portions of the housing may be injection molded simultaneously in an offset injection molding process. An advantage of such off-set molding is that the second portion of the housing (i.e.: the distal end of the housing) can have a greater radial thickness than the first portion of the housing (i.e.: the proximal end of the housing). This design may be used to provide a distal end of greater radial thickness than the proximal end of the device. As such, the teeth 16 formed by the distal end of the device can be made thicker, thereby providing more torque on contact member 25 of spring 22. A second advantage of having the proximal end of the limiter device be of a smaller diameter than the distal end is that the proximal end of the device does not impinge on other components mounted onto the printed circuit board.

What is claimed is:

1. A mechanical limiter device, comprising:
   a housing having a slot passing at least partially therearound, the slot forming a plurality of teeth in a side of the housing;
   a plunger movable within the housing;
   a biasing mechanism configured to urge the plunger in a proximal direction within the housing; and
   a contact member coupled to the biasing mechanism and extending through the slot in the side of the housing, the contact member being configured to advance past at least one of each of the plurality of teeth in the slot each time the plunger is moved back and forth within the housing.

2. The mechanical limiter device of claim 1, wherein the number of times the device is activated equals the number of pairs of teeth in the slot in the side of the housing.

3. The mechanical limiter device of claim 1, wherein the biasing mechanism is a spring.

4. The mechanical limiter device of claim 3, wherein the contact member is an end of the spring.

5. The mechanical limiter device of claim 3, wherein the spring is receivable into the housing through a side channel in the housing.

6. The mechanical limiter device of claim 5, wherein the side of the housing is configured to receive a pair of carrier pins that extend from an electrical connector, and wherein one of the carrier pins is receivable over the side channel in the housing.

7. The mechanical limiter device of claim 3, wherein the housing is configured to receive an end of the spring into a recess defined in the side of the housing at a proximal end of the housing.

8. The mechanical limiter device of claim 3, wherein the housing is configured to receive the spring into the distal end of the housing in an opening provided in the distal end of the housing.

9. The mechanical limiter device of claim 3, wherein the housing is configured to receive the spring into the side of the housing in an opening provided in the side of the housing.

10. The mechanical limiter device of claim 1, wherein the housing comprises:
  separate first and second portions, and wherein the slot is formed in a space between the first and second portions of the housing.

11. The mechanical limiter device of claim 10, wherein the first and second portions of the housing are off-set injection molded from one another.

12. The mechanical limiter device of claim 1, wherein the housing is made of a nonconducting material.

13. The mechanical limiter device of claim 1, wherein the side of the housing is configured to be received onto a pair of carrier pins that extend from an electrical connector.

14. The mechanical limiter device of claim 13, wherein the side of the housing is further configured to accept carrier pins that are barbed.

15. The mechanical limiter device of claim 13 in combination with an electrical connector, wherein each of the pair of carrier pins are mounted onto a printed circuit board on the electrical connector.

16. The mechanical limiter device of claim 1, wherein a distal end of the plunger protrudes through an opening in the distal end of the housing, and wherein the distal end of the plunger is barbed.

17. The mechanical limiter device of claim 1, wherein the housing is made of plastic.

18. The mechanical limiter device of claim 1, wherein the teeth are coated with an electrically conducting material.

19. The mechanical limiter device of claim 1, further comprising:
  a printed circuit board extending therefrom, wherein the housing of the device is formed integral to the printed circuit board.

20. The mechanical limiter device of claim 19, further comprising:
  a flex circuit mounted onto the printed circuit board.

21. The mechanical limiter device of claim 1, wherein the housing comprises:
  an inner portion made of an electrically non-conducting material; and an outer portion made of an electrically conducting material.

22. The mechanical limiter of claim 21, wherein the slot in the housing is formed by the outer portion of the housing.

23. The mechanical limiter device of claim 21, wherein the outer portion of the housing further comprises:
  a tab disposed at the distal end of the housing, the tab being configured to hold the distal end of the biasing mechanism.

24. The mechanical limiter device of claim 21, further comprising:
  a contact pin disposed within the housing, wherein the contact member touches the contact pin when the contact member has advanced past each of the plurality of teeth in the slot.

25. The mechanical limiter device of claim 24, wherein the contact pin is held in position by deformable tabs on the inner portion of the housing.

26. The mechanical limiter device of claim 21, further comprising:
  a cut-out section near the distal end of the outer portion of the housing, the cut-out section dimensioned to receive a distal end of a spring therein, wherein the proximal end of the spring is the contact member.

27. The mechanical limiter device of claim 21, wherein a proximal end of the housing has a chamfered edge.

28. The mechanical limiter device of claim 1, further comprising:
  a printed circuit board extending therefrom, wherein the proximal end of the plunger comprises an electrically conductive material, and wherein the proximal end of the plunger is in contact with the printed circuit board prior to distally advancing the plunger, and wherein the proximal end of the plunger is not in contact with the printed circuit board after the plunger has been distally advanced.

29. The mechanical limiter device of claim 1, further comprising:
  a contact pin disposed on the printed circuit board, wherein the contact member touches the contact pin when the contact member has advanced past all of the plurality of teeth in the slot.

30. The mechanical limiter device of claim 1, wherein movement of at least one of the contact member and the plunger is used to open a circuit.

31. The mechanical limiter device of claim 1, wherein movement of at least one of the contact member and the plunger is used to close a circuit.

32. The mechanical limiter device of claim 1, wherein movement of at least one of the contact member and the plunger is used to change the inductance, capacitance or resistance of an electrical circuit.

33. A method of limiting the number of uses of an electrical device, comprising:
  advancing a biased plunger into a housing of a mechanical limiter device each time the electrical device is activated, and allowing the biased plunger to retract from the housing each time the electrical device is deactivated, wherein the mechanical limiter device has a contact member extending through a slot in the side of the housing, the slot forming a series of teeth, and wherein the contact member is configured to advance past at least one of each of the plurality of teeth in the slot each time the plunger is moved back and forth within the housing until a deactivating destination is encountered by the contact member, at which point the mechanical limiter device serves to shut off power to the electrical device.

34. The method of claim 33, wherein the electrical device is a medical device.

35. The method of claim 33, wherein movement of the plunger back and forth within the housing causes the contact member to advance into contact with a contact pin at the deactivating destination, thereby either completing or shorting out, or changing the inductance, resistance or capacitance of an electrical circuit.

36. A method of forming a mechanical limiter device, comprising:

forming a first portion of a housing;

forming a second portion of the housing;

assembling the first and second portions of the housing together such that a slot is provided on the side of the assembled housing;

inserting a spring into the housing, said spring being associated with a contact member that extends through the slot in the housing; and inserting a plunger into the housing, the plunger being received within the spring;

wherein the housing is configured to allow the contact member to advance radially around the housing as the plunger is moved proximally and distally in succession within the housing.

37. The method of claim 36, wherein the first and second portions of the housing are injection molded simultaneously in an offset injection molding process.

38. The method of claim 36, wherein assembling the first and second portions of the housing together comprises:

sliding the first and second portions of the housing onto a pair of carrier pins.

39. The method of claim 38, wherein the carrier pins extend from a printed circuit board.

40. The method of claim 36, wherein the inner portion of the housing is formed by injection molding, and wherein the outer portion of the device is formed from metal that is snap fit over the inner portion of the housing.

41. The method of claim 40, further comprising:

installing the mechanical limiter device onto a printed circuit board.

* * * * *